United States Patent
Whitlow et al.

(10) Patent No.: US 9,613,543 B2
(45) Date of Patent: Apr. 4, 2017

(54) ALERT GENERATION AND RELATED AIRCRAFT OPERATING METHODS

(71) Applicant: HONEYWELL INTERNATIONAL INC., Morristown, NJ (US)

(72) Inventors: Stephen Whitlow, St. Louis Park, MN (US); William Rogers, Minneapolis, MN (US); Patricia May Ververs, Ellicott City, MD (US); Santosh Mathan, Seattle, WA (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 276 days.

(21) Appl. No.: 13/965,825

(22) Filed: Aug. 13, 2013

(65) Prior Publication Data

US 2013/0323688 A1    Dec. 5, 2013

Related U.S. Application Data

(62) Division of application No. 12/890,133, filed on Sep. 24, 2010, now abandoned.

(51) Int. Cl.
| | |
|---|---|
| G09B 19/16 | (2006.01) |
| A61B 5/18 | (2006.01) |
| B64D 45/00 | (2006.01) |
| G08B 21/06 | (2006.01) |
| A61B 5/00 | (2006.01) |

(52) U.S. Cl.
CPC ............ G09B 19/165 (2013.01); A61B 5/18 (2013.01); B64D 45/0015 (2013.01); G08B 21/06 (2013.01); A61B 5/746 (2013.01); A61B 2503/22 (2013.01); B64D 2045/004 (2013.01)

(58) Field of Classification Search
CPC ... G09B 9/00; G09B 9/02; G09B 9/08; G09B 19/16; G09B 19/165; A61B 5/18; A61B 5/746; G08B 21/02; G08B 21/06

USPC ..................................................... 434/29–72
See application file for complete search history.

(56) References Cited

U.S. PATENT DOCUMENTS

| | | | |
|---|---|---|---|
| 4,879,542 | A | 11/1989 | Elsey |
| 5,243,339 | A | 9/1993 | Graham et al. |
| 5,900,827 | A | 5/1999 | Graham et al. |
| 6,060,989 | A | 5/2000 | Gehlot |
| 6,097,295 | A | 8/2000 | Griesinger et al. |

(Continued)

FOREIGN PATENT DOCUMENTS

FR        2818932 A1    7/2002

OTHER PUBLICATIONS

Mercedes Tackles Drowsiness: Top Down Auto Blog. Top Down [online]. [Retrieved on Aug. 27, 2010]. Retrieved from Internet: <URL: http://www.sfgate.com/cgi-bin/blogs/topdown/detail?entry_id=43031>.

New Warning System Warns of Driver Drowsiness and Distraction. ScienceDaily [online]. [Retrieved on Aug. 27, 2010]. Retrieved from Internet: <URL: http://www.sciencedaily.com/releases/2009/12/091221130224.htm>.

Wright N, et al.; Vigilance on the Civil Flight Deck: Incidence of Sleepiness and Sleep During Long-Haul Flights and Associated Changes in Physiological Parameters. Ergonomics 2001. Centre for Human Sciences, Defence Evaluation and Research Agency, Farnborough, UK.

(Continued)

*Primary Examiner* — Timothy A Musselman
(74) *Attorney, Agent, or Firm* — Lorenz & Kopf, LLP (57) ABSTRACT

A method of operating an aircraft during a flight is provided. An onboard monitoring subsystem of the aircraft detects that a flight crew member is fatigued, and an automated flight crew training exercise is activated in response to detecting that the flight crew member is fatigued. The flight crew member is then engaged with the automated flight crew training exercise, including instructions intended to alleviate flight crew fatigue.

19 Claims, 5 Drawing Sheets

(56) References Cited

U.S. PATENT DOCUMENTS

| | | |
|---|---|---|
| 6,120,461 A | 9/2000 | Smyth |
| 6,144,901 A * | 11/2000 | Nickles et al. ............... 701/19 |
| 6,188,312 B1 | 2/2001 | Gotauco |
| 6,575,902 B1 | 6/2003 | Burton |
| 6,625,485 B2 | 9/2003 | Levendowski et al. |
| 6,661,345 B1 | 12/2003 | Bevan et al. |
| 6,734,799 B2 | 5/2004 | Munch |
| 7,027,621 B1 | 4/2006 | Prokoski |
| 7,454,313 B2 | 11/2008 | Whitlow et al. |
| 7,680,302 B2 | 3/2010 | Steffin |
| 8,506,305 B2 * | 8/2013 | Graham ............... G09B 7/00 434/118 |
| 2005/0030184 A1 | 2/2005 | Victor |
| 2005/0107716 A1 | 5/2005 | Eaton et al. |
| 2006/0220883 A1 * | 10/2006 | Matos ................... 340/573.1 |
| 2007/0043482 A1 | 2/2007 | Aimar |
| 2007/0063855 A1 | 3/2007 | Maass |
| 2008/0030685 A1 | 2/2008 | Fergason et al. |
| 2008/0291032 A1 * | 11/2008 | Prokhorov ........ B60K 28/066 340/576 |
| 2009/0267777 A1 | 10/2009 | Kumar et al. |
| 2010/0016752 A1 | 1/2010 | Sieracki et al. |
| 2010/0055649 A1 * | 3/2010 | Takahashi et al. ............ 434/66 |
| 2010/0174424 A1 | 7/2010 | Cornell et al. |

OTHER PUBLICATIONS

Duric Z. et al: "Integrating perceptual and cognitive modeling for adapatative and intelligent human-computer interaction" Proceedings of the IEEE, New York, US; vol. 90, No. 7, Jul. 1, 2002; pp. 1272-1289.

EP Extended Search Report for Application No. 11 181 726.8 dated Oct. 16, 2012.

EP Communication for Application No. 11 181 726.8 dated Dec. 20, 2012.

Whitlow, S. et al.; Weighted Assessment of Cognitive Workloads of Team Members Responsible for Execution of an Operation. Filed Oct. 29, 2009 and assigned U.S. Appl. No. 12/608,852.

USPTO Office Action for U.S. Appl. No. 12/890,133 dated Mar. 5, 2013.

USPTO Final Office Action for U.S. Appl. No. 12/890,133 dated Jul. 3, 2013.

EP Examination Report for Application No. 11 181 726.8-1803 dated Sep. 10, 2015.

EP extended Search Report for Application No. 15169453.6-1803/ 2933788 dated Feb. 11, 2015.

\* cited by examiner

ALERT GENERATION AND RELATED AIRCRAFT OPERATING METHODS

CROSS-REFERENCE TO RELATED APPLICATION(S)

This application is a divisional of, and claims priority to, U.S. patent application Ser. No. 12/890,133, filed Sep. 24, 2010.

TECHNICAL FIELD

Embodiments of the subject matter described herein relate generally to vehicle systems and subsystems. More particularly, embodiments of the subject matter relate to a crew alerting system that responds to detected measures of flight crew fatigue.

BACKGROUND

Aircraft pilots and other flight crew members are subject to many factors that can lead to physical or mental fatigue, drowsiness, and inattention. Accordingly, it has been proposed to monitor pilot fatigue during flight using certain flight deck subsystems. For example, recent advances in sensing technology, such as electroencephalographic (EEG) sensors, have dramatically reduced the cost and practicality of monitoring the attentiveness of pilots in real-time during flight. Other proposed approaches involve technologies such as facial expression recognition, eyelid movement analysis, flight deck interaction monitoring, and physical activity monitoring.

Existing systems that monitor pilot fatigue may generate an alarm or a notification when pilot fatigue is detected. These systems, however, do not attempt to re-engage fatigued or inattentive pilots through adapting interactions with the flight deck. Nor do these systems adjust or alter the manner in which the onboard alerting system generates alerts in the flight deck. Accordingly, it is desirable to have an onboard alerting system that reacts in an intelligent manner when pilot fatigue is detected. In addition, it is desirable to have an onboard system that attempts to re-engage a fatigued flight crew member via interaction and mental stimulation. Furthermore, other desirable features and characteristics will become apparent from the subsequent detailed description and the appended claims, taken in conjunction with the accompanying drawings and the foregoing technical field and background.

BRIEF SUMMARY

A method of generating alerts associated with the operation of an aircraft is provided. The method determines, with an onboard alerting subsystem of the aircraft, that an alert needs to be generated. The method continues by obtaining, with an onboard monitoring subsystem of the aircraft, a fatigue level of a flight crew member. An alert is generated with nominal audiovisual characteristics when the onboard monitoring system detects that the fatigue level is indicative of a non-fatigued physiological condition of the flight crew member. In contrast, an alert is generated with enhanced audiovisual characteristics when the onboard monitoring system detects that the fatigue level is indicative of a fatigued physiological condition of the flight crew member.

Another method of generating alerts associated with the operation of an aircraft is provided. This method detects, with an onboard flight crew monitoring subsystem of the aircraft, a fatigue level of a flight crew member. The method continues by determining, with an onboard flight crew alerting subsystem of the aircraft, that an alert needs to be generated. The alert is generated with nominal notification characteristics that are correlated to the detected fatigue level. The method continues by checking, with the onboard flight crew alerting system, whether the flight crew member has responded to the alert in an appropriate manner. In addition, when the flight crew member has not responded to the alert in an appropriate manner, the alert is generated with escalated notification characteristics that convey a higher sense of urgency relative to the nominal notification characteristics.

Also provided is a method of operating an aircraft during a flight. The method involves: detecting, with an onboard monitoring subsystem of the aircraft, that a flight crew member is fatigued; activating an automated flight crew training exercise in response to detecting that the flight crew member is fatigued; and engaging the flight crew member with the automated flight crew training exercise. In one embodiment, the automated flight crew training exercise includes instructions for the flight crew or is otherwise designed to mentally stimulate the crew to mitigate pilot fatigue. The automated flight crew training exercise can therefore be tailored to the current flight context so that the training improves the pilot's operational and situational awareness for the current flight.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

Conventional crew alerting systems for vehicles such as aircraft could be enhanced with the techniques and technologies described herein to improve their effectiveness and to make them respond to the detection of flight crew fatigue. In this regard, the crew alerting system described here monitors one or more members of the flight crew (in particular, the pilot) to determine whether or not fatigue has set in. If the system determines that a flight crew member is fatigued, then the manner in which warnings, cautions, and/or alerts are generated is adjusted to compensate for the fatigued condition. For example, an alert may be generated at an increased volume, at a higher frequency, or using an escalating pattern of tones. In certain embodiments, the system automatically launches one or more flight crew training exercises when it detects fatigue. The training exercises are designed to re-engage the fatigued person and to stimulate mental activity.

The techniques and technologies described here can be deployed with any vehicle, including, without limitation: aircraft; watercraft; road vehicles such as cars, buses, trucks, and motorcycles; spacecraft; trains; subways; specialty equipment (e.g., construction equipment, factory equipment, etc.); trams; and the like. The particular embodiments described below relate to aircraft applications, however, the subject matter is not limited or restricted to such aircraft applications.

Figure 1:
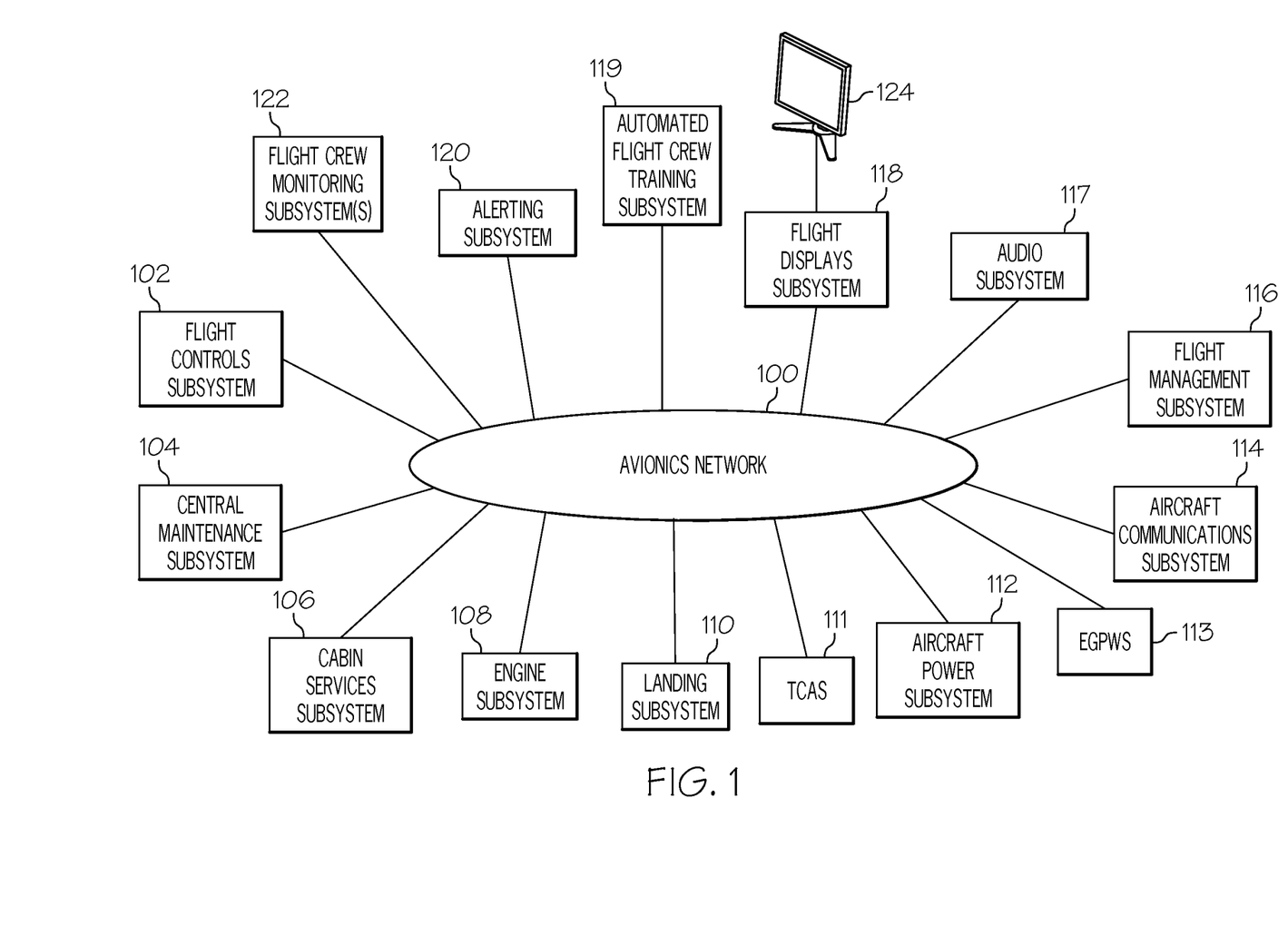
FIG. 1 is a schematic representation of various onboard aircraft subsystems.

FIG. 1 is a schematic representation of various onboard aircraft subsystems that cooperate to form an avionics network 100. This embodiment of the avionics network 100 includes, without limitation: a flight controls subsystem 102; a central maintenance subsystem 104; a cabin services subsystem 106; an engine subsystem 108; a landing subsystem 110; a traffic alert and collision avoidance system (TCAS) 111; an aircraft power subsystem 112; an enhanced ground proximity warning system (EGPWS) 113; an aircraft communications subsystem 114; a flight management subsystem 116; an audio subsystem 117; a flight displays subsystem 118; an automated flight crew training subsystem 119; a flight crew alerting subsystem 120; and at least one flight crew monitoring subsystem 122. The flight displays subsystem 118 includes or cooperates with at least one display element 124. In practice, the avionics network 100 could be implemented with some redundancy. For example, the avionics network 100 might include redundant, independent, and parallel instantiations of one or more subsystems, e.g., the flight displays subsystem 118, the alerting subsystem 120, the flight controls subsystem 102, or the like.

Moreover, the particular subsystems used by an aircraft need not be identical to those depicted in FIG. 1. Indeed, the number, type, and functionality of the onboard subsystems may vary from one airframe to another and from one aircraft to another, and the subsystems shown in FIG. 1 are not intended to limit or restrict the scope of the subject matter described here.

The alerting subsystem 120 is described in more detail below with reference to FIG. 2-4, and the automated flight crew training subsystem 119 is described in more detail below with reference to FIG. 5. The other subsystems utilized by the avionics network 100 need not be specially configured or customized to support the crew alerting and flight crew training techniques, methodologies, and technologies described here. Indeed, certain embodiments of the alerting subsystem 120 and the automated flight crew training subsystem 119 are suitably configured for compliance with legacy avionics subsystems such that those legacy subsystems need not be modified or customized for deployment with the avionics network 100. This description assumes that some or all of the onboard subsystems shown in FIG. 1 are capable of independently monitoring themselves for occurrences of conditions, states, or status that might require issuance of an alert, warning, or caution message. Thus, a given subsystem may be suitably configured to generate and issue alert messages that relate to its operation, functionality, operating state, condition, etc.

In certain embodiments, a given avionics subsystem will have a number of possible alert messages associated therewith. In other words, each subsystem will have a predefined set, list, matrix, table, or array of alert messages or states that could be active or inactive at any given point in time. For example, the engine subsystem 108 may have an associated alert message that relates to an unusual operating condition or status of the engine, another associated alert message that relates to an engine malfunction, and yet another associated alert message that relates to high oil temperature. As another example, the aircraft communications subsystem 114 may have one associated alert message that relates to a malfunctioning antenna, another associated alert message that relates to a datalink function being manually disabled, and yet another associated alert message that relates to a transmit switch being depressed for too long. The number of different alert messages, the contextual meaning of the alert messages, and the conditions under which the alert messages are generated or activated will be defined for each particular avionics subsystem.

The alerting subsystem 120 is responsible for generating and sustaining alerts associated with the in-flight operating status of the host aircraft. In this regard, the alerting subsystem 120 may include or cooperate with a suitably configured caution/warning system such as the EGPWS 113 or another ground proximity warning system, an aircraft warning and caution system, the TCAS 111, or the like. One existing caution and warning system generates four different types of alerts: Warnings, which are the most important or critical; Cautions; Advisories; and Informational alerts. An integrated caution and warning system generates alerts for one or more aircraft subsystems, such as those depicted in FIG. 1. The host aircraft could also utilize any number of independent or federated alerting systems that function in a more isolated manner. For example, one or more of the following may be configured and deployed as an isolated alerting system: a traffic alert system; a GPWS; a datalink message system.

The alerting subsystem 120 can be deployed as a logical processing module in one or more onboard hardware components. In certain embodiments, the alerting subsystem 120 functions as a high level manager and interface for alerts issued by the other onboard avionics subsystems. Thus, the alerting subsystem 120 may be suitably configured to receive the alert messages from the avionics subsystems, process the alert messages, and manage the generation of alert notifications (if needed) while cooperating with the audio subsystem 117 and/or the flight displays subsystem 118. In particular embodiments, the alerting subsystem 120 does not modify certain time-critical alerts such as those from the EGPWS 113 and the TCAS 111.

A flight crew monitoring subsystem 122 used by the host aircraft is suitably configured to monitor the fatigue level of one of more flight crew members. The flight crew monitoring subsystem 122 may include or cooperate with one or more physiological characteristic sensors, imaging sensors, optical sensors, motion detectors, microphones, activity detectors, or the like. For example, the flight crew monitoring subsystem 122 could obtain the fatigue level of a flight crew member based on one or more of the following, without limitation: physiological characteristic data (e.g., blood glucose levels, blood oxygen levels, EEG readings, heart rate data, blood pressure data, body temperature, perspiration levels, respiration rate, etc.); eyelid (blinking) observation data; facial expression observation data; body posture observation data; head position observation data; body movement observation data; user interaction with onboard subsystems such as navigation, communication, or flight control subsystems; microphone data (for monitoring sounds and speech of the user); user activity data; eye position or focus data; and the like. It should be realized that the manner in which the flight crew monitoring subsystem 122 actually measures, detects, determines, or obtains the fatigue level of a person may vary from one deployment of the system to another.

The practical implementation of the flight crew monitoring subsystem 122 will vary depending upon the specific monitoring technology that is utilized. For example, the flight crew monitoring subsystem 122 may include or cooperate with one or more of the following items, without limitation: user-worn or user-carried physiological characteristic sensors or detectors, each of which measures at least one physiological characteristic of the user; a thermometer; a video or still camera; an optical detector; an infrared or ultrasonic detector; physical position sensors (e.g., inertial sensors, accelerometers, gyroscopic sensors); microphones; processors or computing modules that analyze and synthesize user interaction with other onboard subsystems; and the like. These technologies and their related operating principles are known, and, therefore, will not be described in detail here.

Notably, when the flight crew monitoring subsystem 122 determines that a flight crew member is likely to be fatigued, it influences the operation of the alerting subsystem 120 and/or the operation of the automated flight crew training subsystem 119. In this regard, the functionality of the alerting subsystem 120 can be adjusted to compensate for the fatigued condition of the flight crew member, as described in more detail below. Alternatively or additionally, the automated flight crew training subsystem 119 can be activated to launch one or more in-flight training exercises in an attempt to re-engage the fatigued flight crew member and to increase the level of attentiveness in the flight deck. These "fatigue mitigation" approaches are described in more detail below with reference to FIGS. 2-5.

The automated flight crew training subsystem 119 provides embedded training that is designed to improve pilot airmanship by executing tasks that are relevant to the current flight. Accordingly, the training exercises may be influenced by certain flight-specific parameters, such as the flight plan, the current operating condition of the aircraft, the current phase of the flight plan, the current geographic position of the aircraft, etc. As one example, the training subsystem 119 could present exercises, tasks, procedures, questions, and/or problems that relate to aircraft operating skills, pilot skills, flight knowledge, weather condition interpretation, emergency maneuvers, and other skills that might be taught in flight school. The training subsystem 119 could launch an interactive exercise using onboard audiovisual equipment, such as a multi-function display (MFD) or an electronic flight bag (EFB) in such a way that it captures the attention of the flight crew and stimulates mental acuity and attentiveness during phases of flight with low task load, such as cruise. In practice, the training exercises can be hosted by one or more onboard computer systems, and/or by an electronic flight bag.

To ensure that pilots maintain, and in some case improve, their current flight awareness during training, the automated training system will suggest training activities that are relevant to and use flight data from the current flight. For example, modern flight decks perform nearly all of the critical calculations, which has led to the degradation of pilots' manual calculation abilities. Accordingly, the automated training system could request that pilots calculate wind speed, wind direction, magnetic variation, runway crosswinds, and/or true airspeed using parameters from the current flight such as ground speed, course, and heading. The automated training system would compile a training record for each pilot to track their progress in terms of accuracy and time to complete (TTC) calculation. Further, the system could compare pilot performance to peer performance as a means to stimulate their competitive nature and presumably mitigate their fatigued state. The system could also request pilots to explicitly update electronic versions of navigation logs, which is typically performed by modern flight computers and is an important aspect of building and maintaining situation awareness. The system could also request that pilots retrieve and integrate geographical and meteorological information about surrounding airports. While this is a mentally engaging task, it also improves their situational awareness of proximate airports which could provide a significant safety benefit in the event of an abnormal situation. Finally, the system could quiz pilots on topics to help them pass check rides—knowledge tests on aircraft systems, regulations, weather, and the like. These quizzes could re-engage inattentive pilots while helping them maintain proficiency on essential information.

Figure 2:
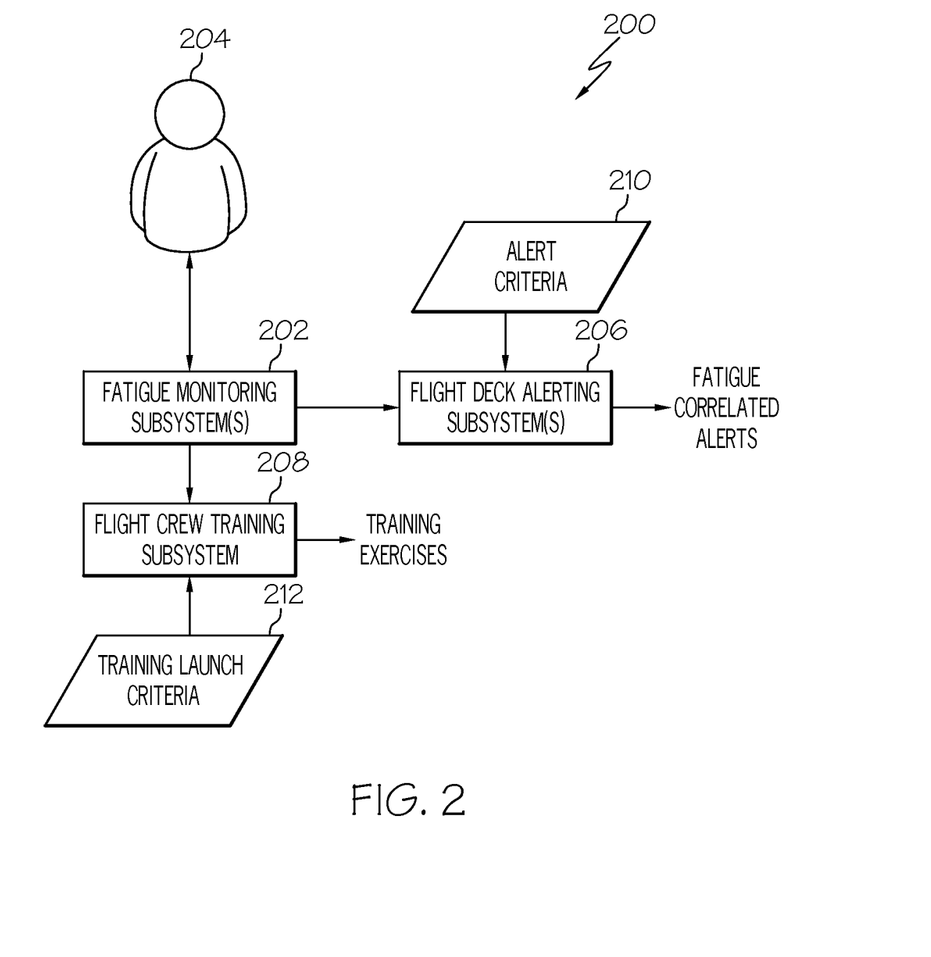
FIG. 2 is a simplified schematic representation of an onboard system that employs a flight crew fatigue monitoring subsystem.

FIG. 2 is a simplified schematic representation of an onboard system 200 that employs a flight crew fatigue monitoring subsystem 202 (configured as described above for the monitoring subsystem 122). The system 200 may use direct and/or indirect techniques to identify when a flight crew member 204 (a pilot, a copilot, or other flight crew member) is likely to be fatigued. As described above with reference to FIG. 1, the system 200 includes or cooperates with at least one flight deck alerting subsystem 206 and at least one flight crew training subsystem 208. For this embodiment, the flight deck alerting subsystem 206 reacts to certain alert criteria 210, which dictates whether or not an alert should be issued. The flight deck alerting subsystem 206 is controlled and configured to generate fatigue-correlated alerts, and the flight crew training subsystem 208 is controlled and configured to provide training exercises for the flight crew member 204.

When the system 200 determines that the flight crew member 204 is fatigued, it can issue notifications regarding the fatigue state or condition, adapt the flight deck environment to re-engage and stimulate the flight crew member 204, modify interaction to ensure the flight crew is attending to alerts and situations, and/or scrutinize flight crew input behaviors for accuracy or errors. The fatigue monitoring subsystem 202 could use an operator state sensing system to directly monitor brain activity associated with the level of fatigue or attentiveness. The fatigue monitoring subsystem 202 could also indirectly infer fatigue or drowsiness or inattention from an observed pattern of user input and activity in terms of latency, error rate, etc. In addition, the flight crew member 204 could be given the opportunity to notify the system 200 that they are fatigued.

Detecting fatigue with EEG sensors is relatively straightforward because the neural signature (alpha waves) are both prominent and distributed across the cortex and, therefore, could be detected by a small number of EEG sensors placed in practical scalp positions for comfortable insertion into an easily donned and doffed headset, integration with aviation communications headset headbands, or integration within other headwear such as a cap. The EEG signals could be processed and transmitted by a combined analog-to-digital conversion module and a wireless transceiver, which may be co-located with the EEG sensors. The EEG signals could be filtered for artifacts and then decomposed into spectral components to identify the power within the alpha band. The system would track the changes in alpha power to provide a near real-time index of flight crew fatigue.

Other direct approaches for measuring fatigue include the use of camera-based systems that monitor head, body, and/or eye movement behavior of the flight crew member 204. Likewise, a small flight deck camera could identify increased blinking behavior, increased "eyes closed" time, or head nodding, which are indicative of drowsiness or fatigue. Another direct method involves the use of a multi-axis accelerometer to detect head movement behavior. An accelerometer could easily detect head nodding behavior, which becomes progressively more pronounced as the individual succumbs to drowsiness. This would also provide a measure of how actively a person is moving visual attention from across the instruments and out the windows (an index that would likely decrease as the flight crew member 204 becomes increasingly fatigued).

Indirect methods could passively monitor the input patterns of the flight crew member 204 to discern a gross activity level, increase in latency or errors to a known even such as an alert, or something simpler such as elapsed time since the last user input. Such an approach would be feasible for aircraft equipped with intelligent flight deck systems that are capable of monitoring and analyzing system events such as alerts, and registering user input across the flight deck.

For both direct and indirect methods, the system 200 could be configured to be sensitive to differing levels of urgency for stimulating a flight crew member across the various phases of a flight. Accordingly, different thresholds could be determined by phase of flight (e.g., takeoff, approach, or cruise).

One embodiment of such a system 200 would employ an open-loop fatigue monitoring subsystem 202 that provides feedback regarding the state of the flight crew member 204. This could support long-haul flights on which pilots share flight responsibility by providing feedback to the crew to support scheduling of rest time among the flight crew members. In addition, EEG is also suited for sleep monitoring and, therefore, could be used to evaluate the quality and quantity of restful sleep. The system 200 could use such information, in addition to knowledge about estimated flight duration and current phase of flight, to intelligently manage the crew duty rotation to maximize the current and future alertness of long-haul pilots.

Another embodiment of the system 200 includes notification capabilities to communicate the condition of the flight crew member 204 to other interested parties such as air traffic control. Such a feature might be particularly desirable for single-pilot aircraft that do not have another flight crew member serving as a backup. By alerting air traffic control, the system 200 could engage the flight crew member 204 in communication to stimulate mental activity and to allow air traffic control to more closely monitor the progress and condition of the fatigued flight crew member 204.

The system 200 could also leverage the knowledge of the differential impact of fatigue on different cognitive and perceptual processes to adapt flight deck interaction parameters in an appropriate manner. In other words, if the system 200 determines that the flight crew member 204 is fatigued, then other onboard systems can be controlled in an appropriate manner to stimulate the flight crew member 204 and to increase the attentiveness of the flight crew member 204. For example, when the system 200 detects flight crew fatigue, it may increase the salience or intensity of auditory and/or visual alerts. Such a system 200 could monitor the person's response to alerts (behaviorally and/or neurologically) to determine whether alert escalation is necessary. If the flight crew member 204 does not respond in an appropriate manner as measured by flight deck input latency and accuracy, of if the person's neural state does not register a transient change in response to an alert, the system 200 will repeat and escalate the audible and/or visual alert characteristics in an attempt to stimulate and engage the fatigued flight crew member 204.

Another embodiment of the system 200 described here employs smart embedded flight crew training, which may be triggered in response to the detection of fatigue by the fatigue monitoring subsystem 202 and/or in response to the satisfaction of other training launch criteria 212. Such a system 200 can contemplate multiple real-time parameters (i.e., the criteria 212) to determine an appropriate and safe time to launch embedded flight crew training that will improve pilot airmanship by executing tasks that are relevant to the current flight. For example, there are many skills that are ubiquitous in flight school and in general aviation, but such skills might diminish after a pilot has completed flight school, especially in view of the high amount of automation found in modern air transport flight decks. In this regard, it may be desirable to provide supplemental or refresher training for pilots at an appropriate time. Indeed, during long flights there are periods where task requirements are so low that pilots might become disengaged and fatigued. During these periods of time, it would be appropriate to launch some engaging training content to re-engage the flight crew member 204, improve airmanship, and increase attentiveness. To further motivate the person undergoing training, there could be a competitive component whereby performance is timed and assessed for accuracy and then compared to the performance of others. In certain embodiments, the system is tuned to maintain flight operations by re-directing the person's attention in the event of off-nominal operations and/or the presence of an alert or caution.

To determine an appropriate time to launch embedded training, the system 200 could consider a number of parameters, criteria, or factors such as one of more of the following, without limitation: phase of flight (take off, climbing, cruise, descent, landing); pilot workload (as estimated by flight deck interaction or direct sensing); and normal operations versus abnormal operations. To determine the appropriate training content, the system 200 might take the following into consideration, without limitation: current aircraft position; relative position within the flight plan, which may dictate the amount of time available for a training session; flight plan details; pilot training history, e.g., target known deficiencies and/or track progress. The training content may be associated with or related to the current flight and it could contemplate potential scenarios, such as locating the nearest airport in the event of an emergency landing.

The system 200 may also be configured to automatically discontinue the training application and to redirect the person's attention to the flight deck when an alert or caution is issued. Moreover, there could be redundant presentation of alerts and cautions within the training application itself to insure that the flight crew immediately turns away from the training exercise and instead focuses on the present situation.

Figure 3:
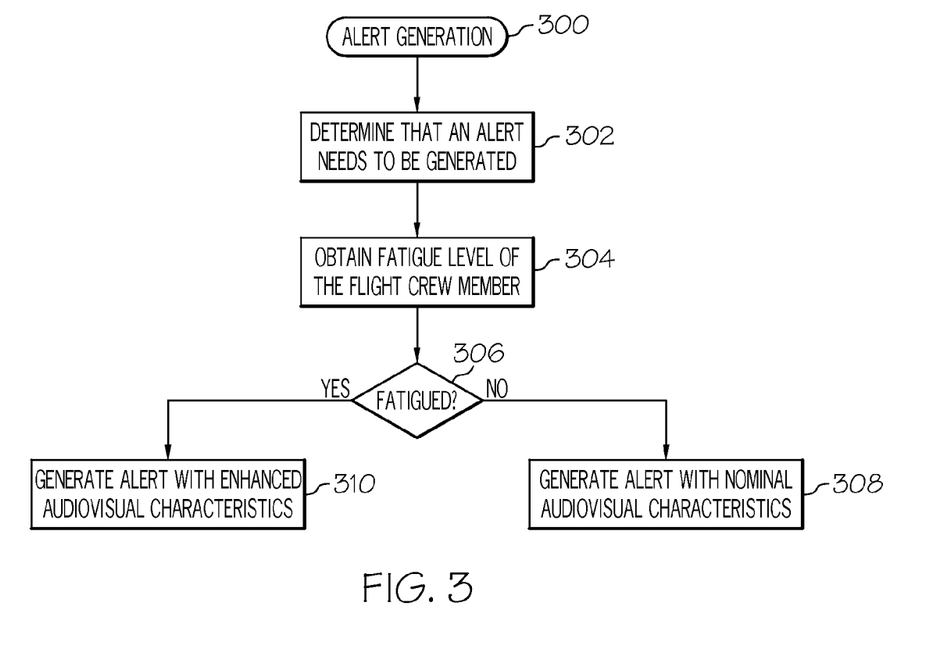
FIG. 3 is a flow chart that illustrates an exemplary embodiment of an alert generation process that contemplates the fatigue level of a flight crew member.
Figure 4:
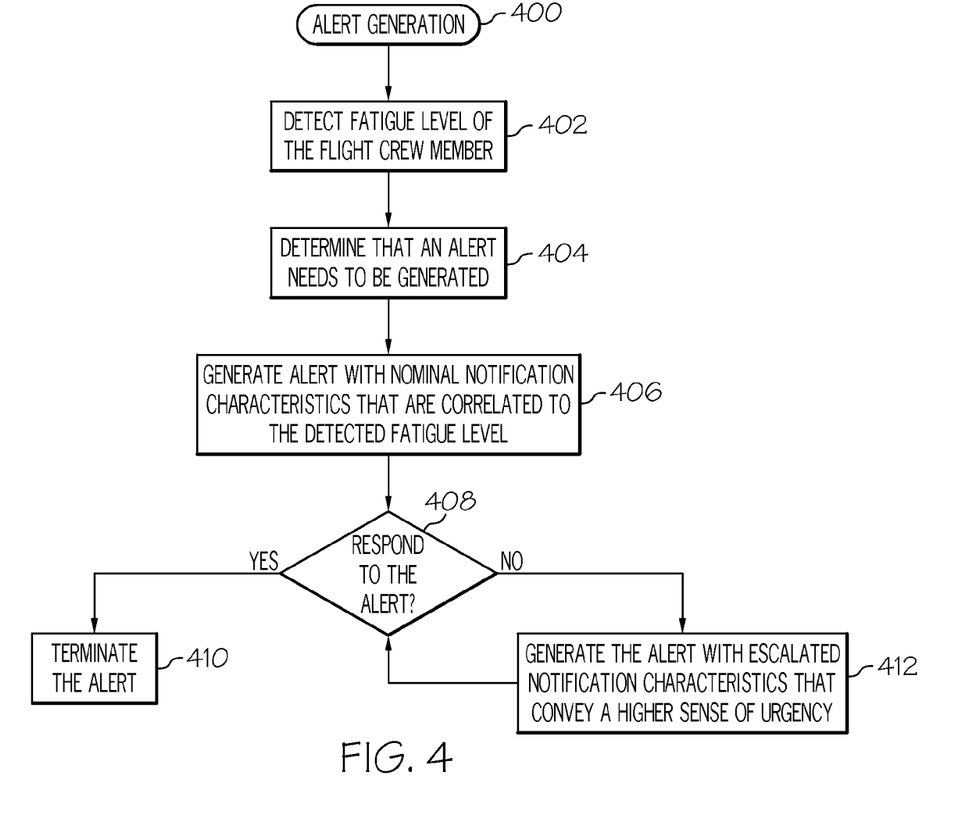
FIG. 4 is a flow chart that illustrates another exemplary embodiment of an alert generation process that contemplates the fatigue level of a flight crew member.
Figure 5:
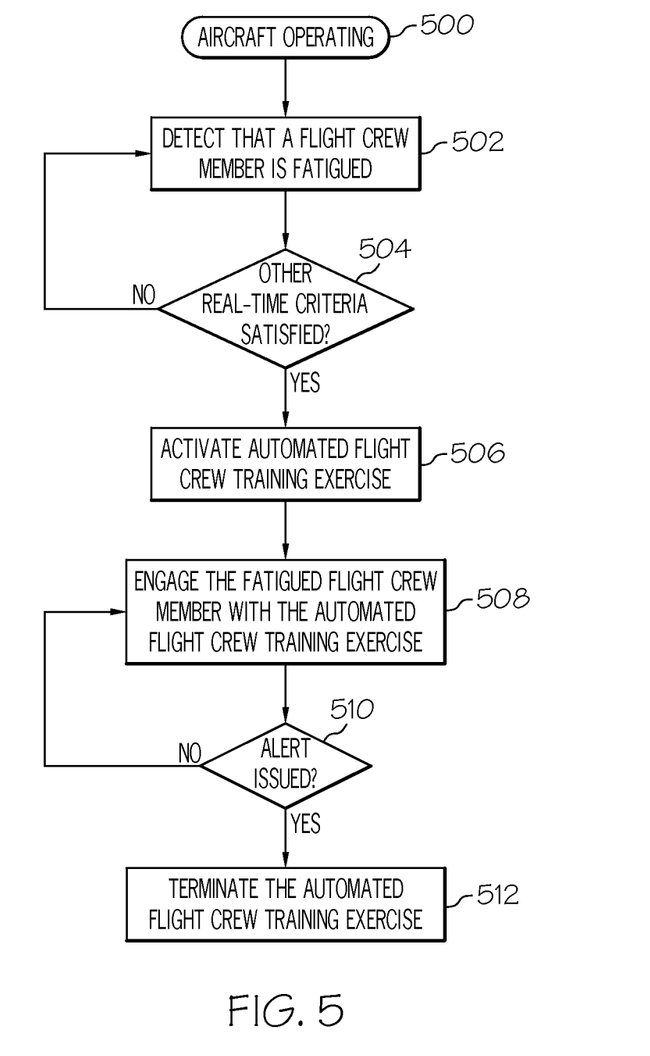
FIG. 5 is a flow chart that illustrates an exemplary embodiment of an aircraft operating process that contemplates the fatigue level of a flight crew member.

Exemplary alert generation and automated training methodologies will now be presented with reference to FIGS. 3-5, which are flow charts that illustrate embodiments of processes that could be performed by an onboard system such as the avionics network 100 or the system 200 described previously. The various tasks performed in connection with a described process may be performed by software, hardware, firmware, or any combination thereof For illustrative purposes, the following description may refer to operations and tasks that might be performed by elements mentioned above in connection with FIG. 1 and FIG. 2. In practice, portions of a described process may be performed by different elements of the described system, e.g., an alerting subsystem, a flight crew monitoring subsystem, a flight crew training subsystem, or the like. It should be appreciated that a described process may include any number of additional or alternative tasks, the tasks shown in the figures need not be performed in the illustrated order, and a described process may be incorporated into a more comprehensive procedure or process having additional functionality not described in detail herein. Moreover, one or more of the tasks shown in the figures could be omitted from an embodiment of its associated process as long as the intended overall functionality remains intact.

FIG. 3 is a flow chart that illustrates an exemplary embodiment of an alert generation process 300 that contemplates the fatigue level of a flight crew member. The process 300 may be performed at any time during aircraft operation, including in-flight, during taxi maneuvers, during stationary testing, etc. The process 300 determines that an alert needs to be generated (task 302), using one or more onboard subsystems or equipment. For example, this determination could be performed with an onboard alerting subsystem of the host aircraft, such as the alerting subsystem 120 shown in FIG. 1. This determination may involve the cooperation with one or more "originating" subsystems onboard the aircraft, i.e., the subsystem(s) that spawned the alert or otherwise caused the alert to be triggered. For purposes of the process 300, an "alert" may be any notification, alarm, warning, message, flag, note, communication, display, sound, vibro-tactile, or any combination thereof that is intended to be received and understood by a member of the flight crew. For example, an alert generated by the process 300 might be one of several types of notifications issued by an aircraft caution and warning system, e.g., a Warning, a Caution, an Advisory, or an Informational message. Moreover, an "alert" may be conveyed using one or more notification, messaging, or indicating techniques and technologies. For example, an alert may be associated with any of the following, without limitation: a sound or a pattern of tones; a voice message; a displayed text message; an indicator light; a flashing pattern or array of lights; tactile feedback transferred via an object that is in contact with the flight crew member (e.g., a vibrating seat, a vibrating instrument panel lever or control stick, or a vibrating headset or helmet); a video clip; a displayed image; or the like.

The process 300 also obtains a fatigue level of a flight crew member (task 304), preferably in real-time or near real-time. In practice, task 304 is performed by at least one onboard monitoring subsystem of the aircraft, such as the flight crew monitoring subsystem(s) 122 depicted in FIG. 1. Thus, task 304 may involve the monitoring and analysis of certain characteristics, physiological conditions, behavior patterns, body position and posture features, and/or other factors that might have some correlation to the level of fatigue, level of drowsiness, level of attentiveness, and/or level of alertness of the monitored flight crew member. Notably, the fatigue level can be derived from or calculated from the sensor information or monitored parameters collected by the onboard system.

In certain embodiments, task 304 involves measuring a physiological characteristic of the monitored flight crew member to obtain a measured physiological characteristic value, and deriving the fatigue level from the measured physiological characteristic value. As mentioned above, the measured physiological characteristic value may be, without limitation: a blood glucose level, a blood oxygen level, EEG data, a heart rate value, a blood pressure value, a body temperature reading, a perspiration level, a respiration rate, or the like. The fatigue level can be derived from the raw physiological characteristic data in any suitable manner. Accordingly, the system could maintain a simple lookup table, compare the raw data to specified threshold values, or use a suitably designed algorithm that translates the raw physiological characteristic data into the desired scale used to measure fatigue levels. For example, lower heart rate values, lower respiration rate values, and lower blood pressure values might be indicative of a relaxed or drowsy state, while high blood pressure values and high perspiration levels might be indicative of an active and attentive state.

In some embodiments, task 304 involves observing a pattern of interactive behavior of the monitored flight crew member, and deriving the fatigue level from the observed pattern of behavior. In this regard, the pattern of behavior may be directly observed by visual means such as a still camera, a video camera, or an image capturing device, or it may be inferred from input and/or feedback (associated with flight deck instrumentation) from the monitored flight crew member. For example, interaction with air traffic control, manipulation of user interfaces, manipulation of aircraft controls, activating buttons, switches, or levers, typing on a keyboard, and similar activities can be monitored and utilized to assess the pattern of behavior. Thus, little or no observed activity might be indicative of a fatigued or tired flight crew member. On the other hand, if normal patterns of behavior are detected (i.e., behavior consistent with an attentive pilot), then the system can assume that the pilot is not fatigued.

Task 304 may also capture body movement activity of the monitored flight crew member, and then derive the fatigue level from the captured body movement activity. The body movement activity could be captured by visual means such as a still camera, a video camera, or an image capturing device, or by other sensors, detectors, or interrogators that might employ infrared, radio frequency, or other techniques. The monitored body movement activity may include, without limitation: eyelid blinking; head nodding; facial expression changes; arm movement; head movement; eye motion; body "slumping" or body shifting; etc. As one example, an utter lack of body movement activity for an extended period of time may indicate that the monitored flight crew member is very fatigued or too relaxed. As another example, if head-nodding or no eye blinking is detected, then the system can infer a high level of fatigue. In contrast, frequent or constant body movement is indicative of a low level of fatigue.

Notably, the measured, detected, and/or sensed parameters are somehow correlated to the level of fatigue of the monitored person. Thus, after the process 300 obtains the fatigue level of the monitored flight crew member, it can determine whether or not the person is likely to be fatigued. For this particular embodiment, if the fatigue level is indicative of a non-fatigued physiological condition of the flight crew member (the "NO" branch of query task 306), then the process 300 generates an alert with nominal audiovisual characteristics (task 308). On the other hand, when the fatigue level is indicative of a fatigued physiological condition of the flight crew member (the "YES" branch of query task 306), then the process 300 generates an alert with enhanced audiovisual characteristics (task 310).

As used here, "audiovisual characteristics" includes audio-only characteristics, visual-only characteristics, or a combination of both audio and visual characteristics. Accordingly, audiovisual characteristics of an alert may be associated with any number of variable parameters including, without limitation: audio volume; audio tone; audio frequency; audio pitch; audio content; display brightness; display (text) content; video content; video playback speed; display color; displayed text size; displayed text font; the position of displayed content; etc.

In certain implementations, task 308 generates an audible alert at a first average volume (which represents nominal notification characteristics), while task 310 generates an audible alert at a second average volume that is higher than the first average volume. Thus, the higher volume represents one type of enhanced or escalated alert. In another embodiment, task 308 generates an audible alert at a constant average volume, while task 310 generates an audible alert at a variable volume, e.g., a variable volume that escalates over time. For this example, the volume may continue to escalate if the system does not detect an appropriate response to the alert. As yet another example, task 308 generates an audible alert that conveys a low sense of urgency, while task 310 generates an audible alert that conveys a high sense of urgency. In this regard, task 308 might generate a pattern of low frequency tones at a relatively low volume, while task 310 might generate a pattern of high frequency tones at a relatively high volume. Alternatively, the sense of urgency could be conveyed by the content of audible speech used in the alert: "pull up" for a low sense of urgency and "PULL UP, PULL UP IMMEDIATELY" for a high sense of urgency).

It should be appreciated that the system could utilize any approach for distinguishing a nominal alert from an enhanced alert. These approaches may include one or more of the following, without limitation: (1) different language, which may be text-based or audible; (2) displaying a visual alert in a less/more visibly conspicuous manner; (3) activating a tactile feedback element at a lower/escalated intensity; (4) activating a tactile feedback element in different detectable patterns; (5) activating less/more warning lamps or indicator lights; (6) employing less/more redundant displays of a visual alert message; (7) presenting an auditory alert in a lower/higher frequency; (8) presenting an auditory alert in a lower/higher volume; and (9) combining multiple parameters such as lower frequency and volume versus higher frequency and volume.

FIG. 4 is a flow chart that illustrates another exemplary embodiment of an alert generation process 400 that contemplates the fatigue level of a flight crew member. Some of the tasks and characteristics of the process 400 are similar or identical to those described above for the process 300, and such common tasks and characteristics will not be redundantly described here in the context of the process 400.

The process 400 detects the fatigue level of a monitored flight crew member (task 402), as described above for the task 304 of the process 300. As mentioned above, the fatigue level may be correlated to one or more detected, measured, sensed, or observed metrics, parameters, phenomena, or the like. For example, the fatigue level may be correlated to: a physiological characteristic of the monitored flight crew member; an observed pattern of behavior of the monitored flight crew member; captured body movement activity of the monitored flight crew member; or the like. The process 400 also determines that an alert needs to be generated (task 404), as described above for the task 302 of the process 300.

The determination made during task 404 triggers the generation of one or more flight deck alerts. In this regard, the process 400 continues by generating an alert with nominal notification characteristics that are correlated to the detected fatigue level (task 406). For example, if the detected fatigue level is relatively low (i.e., the monitored flight crew member is not fatigued), then task 406 will generate the alert in a manner that assumes that the flight crew member is attentive, active, and responsive. In contrast, if the detected fatigue level is relatively high (i.e., the monitored flight crew member is fatigued), then task 406 will generate the alert in a manner that assumes that the flight crew member is not paying attention, is relaxing, or is unresponsive. Thus, the baseline or nominal notification characteristics can be adjusted to contemplate the current state or condition of the monitored flight crew member.

The process 400 checks whether a flight crew member has responded to the alert in an appropriate manner (query task 408). In practice, query task 408 could be performed by the onboard flight crew monitoring subsystem and/or another onboard subsystem, such as the flight deck alerting subsystem. If a flight crew member responds to the alert in an acceptable manner (e.g., by making some type of acknowledgement, by pressing a button, by manipulating a user interface in the required fashion, by communicating with air traffic control, by navigating the aircraft in a particular way), then the alert can be terminated (task 410). If, however, no response is detected after a designated period of time, then the alert will be maintained.

For this particular embodiment, the process 400 continues by generating the alert with escalated notification characteristics that convey a higher sense of urgency relative to the nominal notification characteristics (task 412). Accordingly, the escalated notification characteristics will be different than the nominal notification characteristics, as perceived by the occupants of the flight deck. As explained above for the process 300, the continued alert may exhibit any number of enhanced or escalated notification characteristics, including, without limitation: an escalated volume relative to the alert with nominal notification characteristics; spoken or synthesized language that differs from the language used for the alert with nominal notification characteristics; increased visible conspicuousness; escalated tactile feedback intensity; escalated or different tactile feedback pattern; escalated audio frequency of the alert tone(s); increased "beeping" rate of alert tones; etc.

Although not required, the illustrated embodiment of the process 400 maintains the escalated alert or further escalates the notification characteristics of the alert until a flight crew member responds to the alert in an appropriate manner. Thus, the audiovisual notification characteristics of the alert can be adjusted any number of times until the flight crew responds in a satisfactory manner. In this regard, the escalation of the alert characteristics is utilized to convey an increased and ongoing sense of urgency until someone in the flight deck reacts and responds to the alert.

FIG. 5 is a flow chart that illustrates an exemplary embodiment of an aircraft operating process 500 that contemplates the fatigue level of a flight crew member. The process 500 can be used to automatically launch embedded flight crew training applications, programs, or routines during a flight. The process 500 may begin by detecting that a flight crew member is fatigued (task 502). Task 502 could leverage the fatigue monitoring techniques and approaches described above with reference to FIGS. 1-4.

For purposes of the process 500, flight crew fatigue serves as one triggering mechanism or threshold that influences the launching of embedded training. For this embodiment, however, detected fatigue is only one factor that is considered before launching in-flight training. In this regard, the process 500 may also check whether other real-time criteria associated with the operation of the aircraft has been satisfied (query task 504). This could also be triggered preemptively in situations where cockpit activity is low, and the likelihood of drowsiness (induced by sparse task demands) is high. In practice, the additional real-time criteria can be employed to ensure that the automated training is activated when it is safe to do so, considering the current flight status, aircraft operating conditions, etc. As mentioned previously, these real-time criteria may be associated with various parameters, factors, conditions, or status, such as: the current flight phase; the current workload of the monitored flight crew member; the operating status of the aircraft; autopilot status; etc. If the real-time criteria have not been satisfied, then the process 500 exits or is re-entered at, for example, task 502 (without launching the automated training) If the real-time criteria are satisfied, then the process 500 may continue by activating an automated flight crew training exercise (task 506).

Notably, the system engages (mentally and/or physically) the flight crew member with the automated flight crew training exercise (task 508), with the goal of stimulating the flight crew member to raise the person's level of attentiveness. For example, the flight crew training exercise may be "customized" such that it includes tasks to be performed by the flight crew member, instructions to be followed by the flight crew member, and/or problems to be solved by the flight crew member, at least some of which are relevant to the current flight. The relevancy of these types of problems and exercises might capture the person's attention better than subject matter that is wholly unrelated to the current flight. Examples of activities and exercises are described in more detail above.

It should be appreciated that in-flight training will be launched and carried out under safe flight conditions that do not normally require much flight crew involvement, flight deck interaction, or communication with air traffic control. Moreover, automated in-flight training should have a low priority relative to other tasks, commands, and actions associated with the operation and control of the aircraft. In this regard, the process 500 may check for the issuance of flight crew alerts (query task 510). If an alert is issued, the process 500 terminates or "pauses" the automated flight crew training exercise (task 512) to enable the flight crew to shift its attention to the alert. If no alert is detected, then the automated training exercise may continue. Of course, there may be other conditions, operating states, or criteria that will influence whether or not the automated flight crew training continues, terminates, or pauses. For example, a high frequency or amount of ATC communication would be indicative of a period when the pilot should be paying attention to communication and, therefore, detection of such ATC communication terminate the training Other situations or scenarios that might trigger the termination of training include, without limitation: approaching significant weather; communications received via data link; proximity to descent; and entering the approach corridor for flight. In general, the automated flight crew training exercise can be terminated upon detection of any predetermined or designated termination conditions.

A practical system deployment could deploy any of the processes 300, 400, 500 (individually or in combination). Accordingly, the alert escalation techniques could be implemented in conjunction with the automated flight crew training, both of which involve the monitoring of flight crew fatigue. Moreover, aspects of processes 300, 400 could be merged together in a practical embodiment if so desired.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of operating an aircraft during a flight, the method comprising:
   detecting, with an onboard monitoring subsystem of the aircraft, that a flight crew member is fatigued;
   activating, by audiovisual equipment onboard the aircraft, an automated flight crew training exercise in response to detecting that the flight crew member is fatigued;
   presenting, via the audiovisual equipment, the flight crew member with the automated flight crew training exercise for completion, wherein the automated flight crew training exercise comprises one or more tasks including content to improve pilot airmanship and to increase attentiveness of the flight crew member, and wherein the one or more tasks are associated with flight school skills and general aviation skills;
   receiving input from the flight crew member to complete the one or more tasks; and
   compiling a training record for the flight crew member, based on the input, wherein the training record includes at least a time to complete the one or more tasks by the flight crew member and accuracy of completion of the one or more tasks by the flight crew member;

wherein the one or more tasks comprises calculations to be performed by the flight crew member, wherein the calculations are performed using input parameters from the flight; and wherein the calculations comprise one or more of wind speed calculations, wind direction calculations, magnetic variation calculations, runway crosswinds calculations, and true airspeed calculations.

2. The method of claim 1, further comprising:

evaluating real-time criteria to determine an appropriate time to activate the automated flight crew training exercise;

wherein the real-time criteria is associated with low cockpit activity and sparse task demands.

3. The method of claim 1, further comprising:

evaluating real-time criteria to determine an appropriate time to activate the automated flight crew training exercise;

wherein the real-time criteria comprises one or more of a current flight phase, a current workload of the flight crew member, an operating status of the aircraft, and an autopilot status.

4. The method of claim 1, further comprising terminating the automated flight crew training exercise upon detection of predetermined termination conditions.

5. The method of claim 4, wherein the predetermined termination conditions comprise detection of a high frequency of air traffic control (ATC) communication.

6. The method of claim 4, wherein the predetermined termination conditions comprise detection of approaching significant weather.

7. The method of claim 1, further comprising:

evaluating a relative position within a flight plan to calculate an amount of time available for completion of the automated flight crew training exercise; and determining appropriate training content for the automated flight crew training exercise, based on the calculated amount of time available.

8. The method of claim 1, further comprising:

evaluating a training history of the flight crew member to identify deficiencies; and determining appropriate training content for the automated flight crew training exercise based on the identified deficiencies.

9. The method of claim 1, further comprising:

timing performance of the flight crew member during completion of the automated flight crew training exercise, to obtain a time result;

comparing the time result to a plurality of peer time results to obtain a time competition result; and storing the time competition result in a training record for the flight crew member.

10. The method of claim 1, further comprising:

assessing performance of the flight crew member following completion of the automated flight crew training exercise, to obtain an accuracy result;

comparing the accuracy result to a plurality of peer accuracy results to obtain an accuracy competition result; and storing the accuracy competition result in a training record for the flight crew member.

11. The method of claim 1, wherein activating the automated flight crew training exercise is performed in response to satisfaction of real-time criteria associated with operation of the aircraft.

12. An aircraft onboard system for increasing flight crew member attentiveness, the system comprising:

a flight crew fatigue monitoring subsystem, configured to detect a fatigue level of a flight crew member; and a flight crew training subsystem, configured to:

activate an automated flight crew training exercise in response to detecting that the flight crew member is fatigued; and present the flight crew member with the automated flight crew training exercise for completion, wherein the automated flight crew training exercise comprises one or more tasks including content to improve pilot airmanship and to increase attentiveness of the flight crew member, and wherein the one or more tasks are associated with flight school skills and general aviation skills;

receive input from the flight crew member to complete the one or more tasks; and compile a training record for the flight crew member, based on the input, wherein the training record includes at least a time to complete the one or more tasks by the flight crew member and accuracy of completion of the one or more tasks by the flight crew member;

wherein the automated flight crew training exercise comprises retrieval and integration of geographical and meteorological information associated with surrounding airports.

13. The aircraft onboard system of claim 12, wherein the one or more tasks comprise completion of knowledge tests on aircraft systems and regulations.

14. The aircraft onboard system of claim 12, wherein the one or more tasks comprise performing critical calculations for flight.

15. The aircraft onboard system of claim 12, wherein the flight crew training subsystem is further configured to:

detect presence of an alert within the aircraft onboard system; and redirect attention of the flight crew member upon detection of the alert.

16. An aircraft onboard system for increasing flight crew member attentiveness, the system comprising:

a flight crew fatigue monitoring subsystem, configured to detect a fatigue level of a flight crew member; and a flight crew training subsystem, configured to:

activate an automated flight crew training exercise in response to detecting that the flight crew member is fatigued; and present the flight crew member with the automated flight crew training exercise for completion, wherein the automated flight crew training exercise comprises one or more tasks including content to improve pilot airmanship and to increase attentiveness of the flight crew member, and wherein the one or more tasks are associated with flight school skills and general aviation skills;

receive input from the flight crew member to complete the one or more tasks; and compile a training record for the flight crew member, based on the input, wherein the training record includes at least a time to complete the one or more tasks by the flight crew member and accuracy of completion of the one or more tasks by the flight crew member;

wherein the flight crew training subsystem is further configured to:

contemplate potential scenarios of a current flight; and select the automated flight crew training exercise for activation based on the potential scenarios.

17. The aircraft onboard system of claim 16, wherein the one or more tasks comprise completion of knowledge tests on aircraft systems and regulations.

18. The aircraft onboard system of claim 16, wherein the one or more tasks comprise performing critical calculations for flight.

19. The aircraft onboard system of claim 16, wherein the flight crew training subsystem is further configured to:
   detect presence of an alert within the aircraft onboard system; and
   redirect attention of the flight crew member upon detection of the alert.

* * * * *

UNITED STATES PATENT AND TRADEMARK OFFICE
CERTIFICATE OF CORRECTION

PATENT NO. : 9,613,543 B2  
APPLICATION NO. : 13/965825  
DATED : April 4, 2017  
INVENTOR(S) : Whitlow et al.

Page 1 of 1

It is certified that error appears in the above-identified patent and that said Letters Patent is hereby corrected as shown below:

In the Claims

Column 16, Lines 66-67 Claim 16 "select the automated flight crew training exercise for activation based on the potential scenarios." should be -- select the one or more tasks for presentation to the flight crew member based on the potential scenarios. --

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*